(12) United States Patent
Elkind

(10) Patent No.: US 6,503,085 B1
(45) Date of Patent: Jan. 7, 2003

(54) USE OF VIRTUAL REALITY AND DESK TOP COMPUTER FORMATS TO DIAGNOSE EXECUTIVE DYSFUNCTIONS

(76) Inventor: James Elkind, 76 Cotton St., Newton, MA (US) 02158

( * ) Notice: Subject to any disclaimer, the term of this patent is extended or adjusted under 35 U.S.C. 154(b) by 46 days.

(21) Appl. No.: 09/689,145

(22) Filed: Oct. 12, 2000

Related U.S. Application Data (63) Continuation-in-part of application No. 09/239,284, filed on Jan. 29, 1999, now Pat. No. 6,149,586.
(60) Provisional application No. 60/072,992, filed on Jan. 29, 1998.

(51) Int. Cl.[7] .......................... G09B 19/00; A61B 5/00; A61B 10/00; A63B 67/00; A63B 71/00
(52) U.S. Cl. ...................... 434/236; 600/300; 128/920; 434/118; 273/461
(58) Field of Search ................................ 600/300–301; 128/920–925, 897–898; 434/236, 29, 419; 273/459–461, 317.1

(56) References Cited

U.S. PATENT DOCUMENTS

| | | | | |
|---|---|---|---|---|
| 4,086,710 A | * | 5/1978 | Craine | 434/236 |
| 5,736,986 A | * | 4/1998 | Sever, Jr. | 345/419 |
| 5,782,639 A | * | 7/1998 | Beal | 434/29 |
| 5,807,114 A | * | 9/1998 | Hodges et al. | 434/236 |

* cited by examiner

*Primary Examiner*—Max Hindenburg
*Assistant Examiner*—Michael Astorino
(74) *Attorney, Agent, or Firm*—David D. Lowry; Joseph P. Quinn; Brown Rudnick Berlack Israels LLP (57) ABSTRACT

The present invention includes using computer simulation and virtual reality (VR) tests for determining categories of neuropsychological dysfunctions, including executive dysfunctions. A test subject interacts with a computer generated simulated environment according to a predetermined test script. The test script presents a simulated environment of sight and sound which can closely mirror a real activity, such as daily routines performed by everyone; or an environment such as a game played by the subject. The test script is designed to present situations where subjects with executive dysfunctions will interact and make decisions which indicate the dysfunctions. During the testing, other physiological measurements may be measured and recorded, including subject respiration, heart rate, blood pressure, skin changes etc. The results of the testing are interpreted by scoring the subject's reactions, and provide an indication of the subject's dysfunctioning. These results may be used along with other standardized tests as known in the art, to produce a complete prognosis.

20 Claims, 3 Drawing Sheets

USE OF VIRTUAL REALITY AND DESK TOP COMPUTER FORMATS TO DIAGNOSE EXECUTIVE DYSFUNCTIONS

CROSS REFERENCE TO RELATED APPLICATIONS

The present application is a continuation-in-part of U.S. application Ser. No. 09/239,284 filed on Jan. 29, 1999 by Elkind, now U.S. Pat. No. 6,149,586 which claims the benefit of U.S. Provisional Application Serial No. 60/072,992 filed on Jan. 29, 1998, the entire contents of these applications are hereby incorporated herein by reference.

BACKGROUND

1. Field of the Invention

The present invention relates generally to systems and methods for testing neuropsychological dysfunction and, more particularly, to systems and methods for diagnosing neuropsychological dysfunction that employ computer simulated environments.

2. Description of the Related Art

Continuing medical and technological advances have resulted in more prematurely born infants living than ever before, and current research has shown that 25% of those infants carry mild to moderate disabilities. In addition, there are large numbers of young adults who suffer brain damage and cognitive dysfunctions caused by head injuries. It is estimated that more than seven million children between the ages of six and twenty-one, and approximately twenty million adults over twenty-one have either mental retardation, learning disabilities, or traumatic brain injuries with attendant cognitive deficits. One category of cognitive deficits are known as executive dysfunctioning.

Executive Functions are those functions which significantly determine the extent to which a person exhibits appropriate and responsible adult behavior. They enable individuals to establish priorities, make decisions, or alter a course of action when intervening circumstances require action modifications. Of the cognitive defects that impact daily functioning of people with neurological deficits, executive functions effect the everyday personal, interpersonal, and work related behaviors in ways that critically impact interpersonal relationships and functional abilities in the areas of independent living and work.

Four major components of executive functioning are volition, planning, purposeful behavior and effective performance.

Volition is an individual's will, agency, choice, etc., that emanates from knowing what one wants and contains the motivation to gratify those wants and desires.

Planning reflects one's ability to plan and execute a sequential series of goal directed behaviors. Competent planning demonstrates skills in organizing, thoughts and plans, securing and working with the necessary people, equipment, tools, etc. Effective planning also requires mental flexibility when unexpected obstacles intervene.

Purposeful behavior reflects the ability to initiate purposeful sequentially executed behaviors that demonstrate awareness of self, others, and the environment. It involves the person's capacity to employ flexibility when circumstances require modifications in goal and adoption plans.

Effective performance indicates the capacity to observe, correct, and regulate one's own behavior, affect speed of operation, and thoroughness of performance. Attitude and judgment or performance thoroughness are important to observe and assess. (Lezak, 1995, PP 650–677).

Disorders of executive functioning can be reflected by inadequate self care skills, in (difficulty managing) or spending money prudently, and problems initiating and completing intentional, goal-directed, self monitoring actions. There is typically evidence of all or some of the following deficiencies:

1. Problems with volition and initiating behavior can be reflected by a lack of motivation, the inability to initiate intentional actions, and may involve difficulties in executing and sustaining focused, goal-directed actions. There often is a lack of self awareness and sensitivity towards others.

EXAMPLE 1

A person is aware of the need to shower, brush teeth, comb hair and wear clean clothes, but is unable to do this regularly unless another person remains present and directs each step of the morning hygiene and personal care routine.

EXAMPLE 2

A man's inability to stop flooding every new girl friend with gifts, invitations and phone calls results in his inevitably losing every newly initiated relationship. The man always experiences sorrow and remorse for causing the woman enough distress to break-up with him. However, regardless of the guidance or reminders of behavioral rules, the man can not refrain from resorting to the same behaviors when starting out with a new girlfriend.

2. Planning deficits are often related to poorly organized action sequences that include the necessary people and resources to reach the intended goal. The insufficient awareness of the relationship between planning, actions and outcome poses problems when these individuals are confronted with the unanticipated repercussions of their poor planning and inability to implement alternative strategies.

EXAMPLE 3

A woman wants to complete her college education. She registers for courses that are too demanding and beyond her academic skills. She is unable to attend classes, maintain part time employment, and she refuses any advice and suggestions from college counselors or professionals. Their recommendation that fewer and less demanding courses be considered is ignored and the woman drops out of school, blaming her failures on the teachers and "system."

EXAMPLE 4

A person wants to live in his own apartment and "run his own life." However, he makes no attempt to earn a steady job which would enable him to afford an apartment and the self maintenance expenses. While he sees the relationship between wanting an apartment, needing the money to pay rent, and getting a regular paying job, he makes no independent attempt to look for a job or contact a vocational rehabilitation agency.

3. Inability to execute purposeful behaviors is characteristically reflected in impulsive actions disinhibited speech and/or conduct where the person is unable to contain irrelevant or reflexive responses. Difficulties also occur when routinely executed functions no longer are appropriate and the person cannot modify his plan or behavior according to those changes (Levinson, 1996).

EXAMPLE 5

A young clerical employee talks with his financial tutor about taking a week's vacation to Disney World. He wants to travel by airplane, stay in a hotel, and visit the park. Discussions reveal neither an awareness of the planning process, nor a realistic idea of the involved costs. His desire to contact airlines, hotels, and the park without assistance were initially respected. A lack of results led the counselor and the employee into developing a written money saving and planning process. With frequent case-manager visits, he was able to follow the written directions.

4. Ineffective performance refers to the difficulty a person has observing, modifying and regulating his/her behavior.

EXAMPLE 6

A man with average intelligence receives financial counseling regarding budgeting, bill paying, managing his check book and use of funds for leisure activities and life essentials. Despite agreed upon strategies and guidelines geared to help the person live within his financial boundaries, he usually cashes pay checks immediately and spends seventy-five percent of his earnings despite bills, obligations and other expenses which require attention.

5. Perseverations are behaviors or verbalizations which, driven by internal, unconscious and/or neurological determinants, continue well beyond interpersonal and/or circumstantial appropriateness.

EXAMPLE 7

A person with cognitive disabilities is taught how to greet guests who come to the door. However, once he introduces himself, asks the person's name, and says "pleased to meet you" he persists in going through the script long after it is applicable. (This behavior also may reflect impulsivity.)

6. Impulsive behaviors are those that occur without regard to contextual or social appropriateness without regard for consequences.

EXAMPLE 8

A person living from a fixed income and budget goes food shopping. He brings his shopping list and the usual amount of money. While selecting items from this list he is approached by a promoter to purchase a manual food processor on a ten day, fully refundable trial. The person makes the purchase, is unable to complete the necessary food purchases and blames the independent living instructor for not having him bring sufficient funds. (Also, inadequate planning and self monitoring may contribute.)

7. Diminished self and interpersonal awareness exists when a person is unaware of how his/her behavior impacts another person, is (in)appropriate to the context and demonstrates little self awareness as well as reduced capacity to alter behavior or acknowledge it.

EXAMPLE 9

A person applies for and interviews for a job. During the meeting, the applicant admonishes the interviewer for being late. When job duties are described the applicant complains that there is too much time required filling in as a receptionist. The applicant did not notice the interviewer check and re-check his watch, cross his arms, and interrupt the applicant mid sentence when the applicant scorned the salary. Later when asked how the interview proceeded, the candidate disclaimed any interest in the job, saying that the salary and hours weren't worth it.

8. Inability to switch conceptual frameworks refers to an individual's difficulty shifting attention from one feature of the environment to another. With impaired executive functioning, an individual finds it difficult to respond in optimal ways. For example, successful employment and social relationships require the ability to recognize and respond to feedback, the ability to control impulses, and a certain amount of cognitive flexibility. Obviously, assessment and rehabilitation techniques that most closely reflect the real world will prove most beneficial to the millions of individuals suffering from cognitive and neurological dysfunction.

As these examples show, a person with executive dysfunction may outwardly appear to function with normal skills, but have dysfunctions which manifest during everyday routines. Diagnosing these dysfunctions is problematic for the very reason that they are often not observable from a typical lab testing situation. A person may function perfectly during analysis and review of activities. It is only when they are engaged in daily activities that these dysfunctions appear.

Attempting to determine executive dysfunctions from observing the person during daily situations is problematic. First, there is the time and expense of accompanying and observing the person during their daily routines. Such observation may take several days or weeks to readily determine a pattern of executive dsyfunctions. Further, the presence of the observer can affect the results, wherein the person will modify their behavior or take different actions because they know the observer is there. For dysfunctional persons attempting to autonomously function in the real world, the presence of an observer is a self-conscious reminder to behave "correctly". Further, when a support person is present, the dysfunctional individual can defer to them for advice instead of making their own decisions.

SUMMARY

Accordingly, the present invention includes a system and method for testing a subject for determining neuropsychological dysfunctions, including executive dysfunctions, using computer simulated reality to provide more accurate assessments of a subject's executive deficits. The illustrative embodiments of the present invention include a predetermined test scenario script, to provide a test scenario to the subject. A scenario simulation component on the computer, produces a simulated reality environment based on said predetermined test scenario script, which is displayed to the subject using visual systems such as monitors and head mounted displays (HMDs).

The subject interacts and responds to the environment by various input devices including keyboards, joysticks, pointing devices, tactile and sensory gloves, etc. A test scenario result reviewing component, accepts the input from the subject in response to the subject interacting with the simulated reality environment, and determines result information based on analyzing the subject's interactions. The result information includes processing by standard techniques, including statistical analysis, to determine a score.

The system also accepts, as input, physiological measurements from the subject.

The scenarios provide more ecologically valid scenes that simulate real life situations and will identify and predict, with greater applicability to real life, validity and reliability, executive functioning disabilities and their likely impact on daily living activities. Dysfunctions such as, for example, difficulties in correctly identifying categories of sorting, perseverative responses, inability to shift concepts/sets, etc., are analyzed and identified to determine the existence and significance of any deficits in executive functioning.

Advantages of the present invention include an objective, repeatable test standard for gauging individuals and measuring results. Computer simulations allow standardized tests to be presented to individuals, allowing comparison of results. The results are more valid and reliable than existing paper and pencil tests that are administered by different examiners, and scored by different interpreters. The measured results, obtained in accordance with the present disclosure, demonstrate the nature and extent of the cognitive disabilities. Further, the results translate, because of their ecological validity, more easily into rehabilitation training (whether by Virtual Realty (VR) "sessions" or other methods) and transfer into real world environments.

Moreover, a fully developed test scenario is low in cost to administer. Actors and props are not necessary to enact situations for observing a test subject's reactions.

Another advantage of the present invention is a "safe" environment for test subjects to interact in real-world situations without harm or loss of money. Test parameters such as background noise can be readily adjusted to requirements for the test subject. Further, since the test subject is typically limited in the movement they can perform during the test, it is easy to monitor the test subject including physiological measurement instruments, such as, for example, blood pressure, EEG, EKG, galvanic skin sensors, eye, hand movement, etc.

In one particular embodiment, in accordance with the present disclosure, a system for testing neuropsychological dysfunction is provided which includes at least one predetermined test scenario and an interactive computer generated simulated environment, based on the predetermined test scenario. A test scenario processor communicates with the interactive computer generated simulated environment and is configured to receive input from a subject interacting with the interactive computer generated simulated environment in order to determine a neuropsychological dysfunction diagnosis of the subject. The input received from the subject may include physiological measurements.

In an alternate embodiment, the system includes a test administrator input which communicates with the test scenario processor. The test scenario processor receives input from a test administrator for modification of the predetermined test scenario.

The interactive computer generated simulated environment may provide at least one question to the subject based on the predetermined test scenario. The question may be modified by the test administrator. The interactive computer generated simulated environment may provide a plurality of questions. Modification may include omission of a portion of the plurality of questions. Further, the system may include a plurality of predetermined test scenarios in which the test administrator may substitute portions of the plurality of test scenarios.

The interactive computer generated simulated environment can include a plurality of questions based on the predetermined test scenario. The test administrator may modify the plurality of questions when the subject's input includes perseverations. The system can also include a plurality of predetermined test scenarios.

In an alternative embodiment, the predetermined test scenario includes a sequence of real life events. In this embodiment, the interactive computer generated simulated environment includes at least one question to the subject based on the sequence of real live events. The sequence of real life events may include a beach scene.

The predetermined test scenario may include a sequence of non-reality events whereby the interactive computer generated simulated environment includes at least one question posed to the subject based on the sequence of non-reality events.

In another alternative embodiment, interactive computer generated simulated environment may be substantially immersive. The interactive computer generated simulated environment may, alternatively, be substantially non-immersive.

A method for testing neuropsychological dysfunction is provided in accordance with the present disclosure. The method comprises the steps of providing at least one predetermined test scenario; producing an interactive computer generated simulated environment based on the predetermined test scenario; interacting the interactive computer generated simulated environment with a subject; receiving input from the subject interacting with the interactive computer generated simulated environment by a test scenario processor communicating with the interactive computer generated simulated reality environment; and determining a neuropsychological dysfunction diagnosis of the subject based on the input received by the test scenario processor.

The method may include the step of producing an interactive computer generated simulated environment which is substantially immersive. Alternatively, the method may include a step of producing a computer generated simulated environment which is substantially non-immersive.

The method may include a step of receiving input from a test administrator for modifying the predetermined test scenario. Further, the step may include a predetermined test scenario which has a sequence of real life events. The interactive computer generated simulated environment may include a plurality of questions to the subject based on the sequence of real life events. In addition, the sequence of real life events may be based on a beach scene.

BRIEF DESCRIPTION OF THE DRAWINGS

The foregoing and other features and advantages of the present invention will be more fully understood from the following detailed description of illustrative embodiments, taken in conjunction with the accompanying drawings in which.

DETAILED DESCRIPTION OF THE EXEMPLARY EMBODIMENTS

Figure 1:
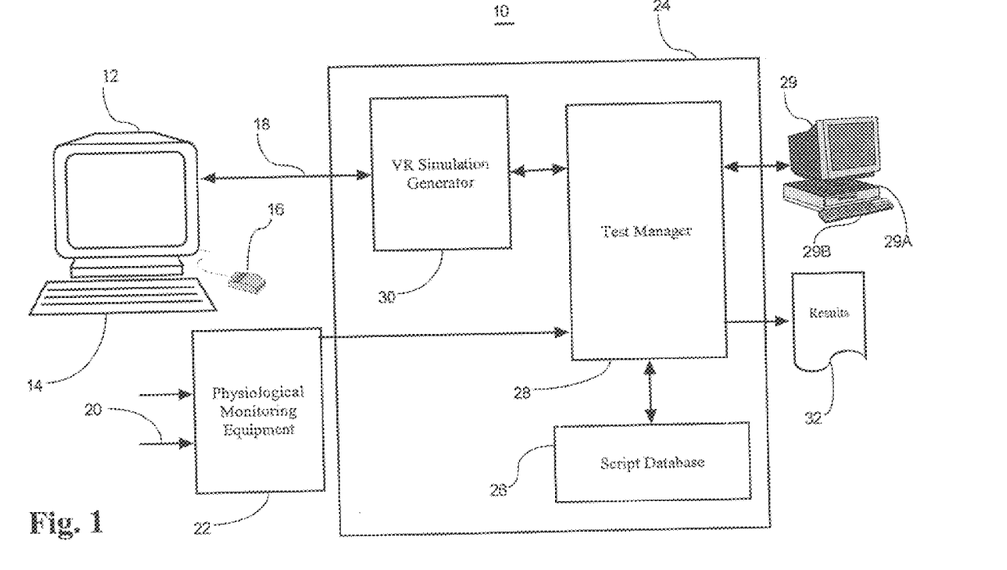
FIG. 1 is a block diagram showing the components of an illustrative testing system in accordance with one embodiment of the present invention.
Figure 2:
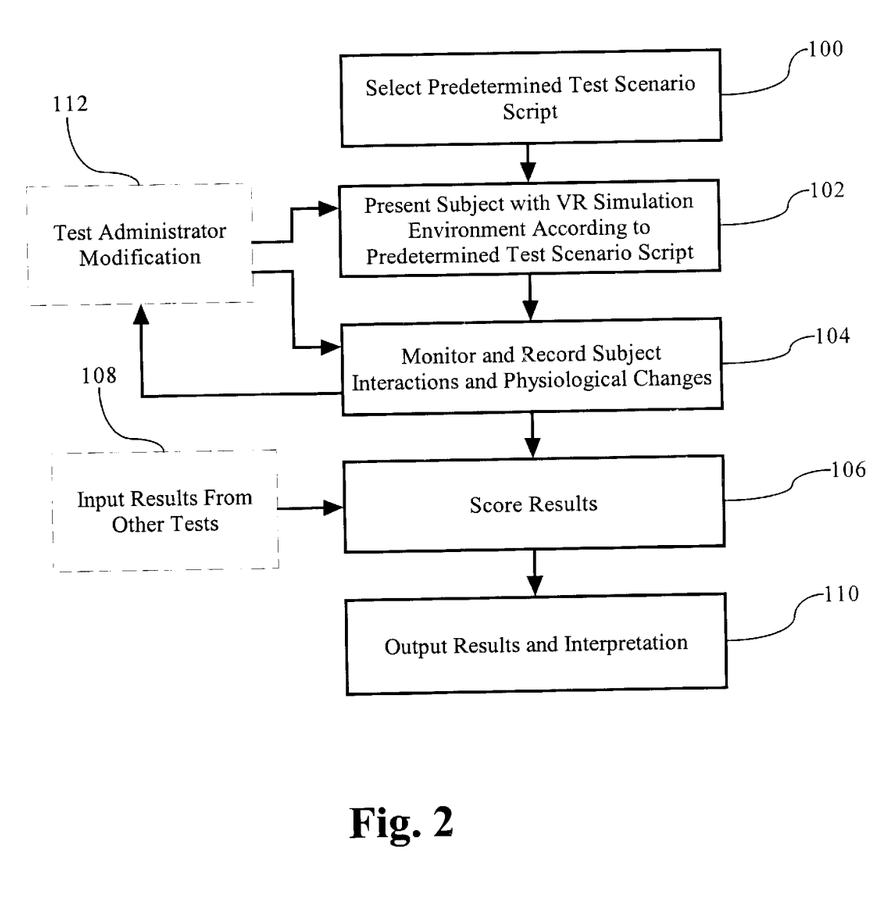
FIG. 2 is a flow chart of the steps performed according to the illustrative testing system of FIG. 1.

The present invention includes using computer simulation and virtual reality (VR) tests for determining categories of neuropsychological dysfunctions, such as, for example, executive dsyfunctions. A system 10 for testing neuropsychological dysfunction in accordance with one embodiment of the present invention is shown in FIGS. 1 and 2.

System 10 includes a predetermined test scenario that is developed for testing neuropsychological dysfunction. The predetermined test scenario is based on a sequence of real life events such as, for example, a casino, beach, office setting, home setting, etc. It is envisioned that the predetermined test scenario may be based on a sequence of non-reality events for creating a fantasy type environment. System 10 may include a plurality of scenarios.

An interactive computer generated simulated reality environment is based on the predetermined test scenario. The computer generated simulated reality environment may be created by various computer systems and a variety of instrumentation used to facilitate interaction with the subject, as will be discussed in greater detail below. The interactive computer generated simulated reality environment provides a plurality of questions based on the predetermined test scenario. These questions facilitate determination of a neuropsychological dysfunction diagnosis through testing. It is envisioned that questions, prompt initiating stimulus, etc., may be configured for various duration of response and/or matching times by the subject.

A test scenario processor communicates with the interactive computer generated simulated reality environment, as will be discussed below. The test scenario processor is configured to receive input from the subject interacting with the interactive computer generated simulated reality environment. Various input devices may be used by the test subject, as will be discussed below. The test scenario processor receives the input to determine a neuropsychological dysfunction diagnosis of the subject.

The test subject views a display monitor 12 of the interactive computer generated simulated reality environment which displays the simulation according to the scenario. The simulated reality environment may include sounds from speakers (not shown).

The subject interacts with system 10 by input devices including a keyboard 14 and a mouse 16. Scenarios for system 10 are developed for use on a standard desk top computer 24 and monitor 12. It is contemplated that predetermined test scenario may be created by various means such as, for example, digital recording, voice-recognition systems, etc., and subsequently and/or simultaneously loaded with computer 24.

Such simulation equipment and methods do not require elimination of awareness of and sensitivity to the surrounding environment. However, wraparound display monitors can be utilized to increase a sense of immersion and exclude greater amounts of the immediate environment. One advantage of the present disclosure employed with a substantially immersive environment is that the subject benefits from real time graphics, i.e., actions of the subject/player will be immediately responded to on monitor 12 which may include a wraparound monitor.

The more immersive the environment, the less relevant outside distractions become. The intensity of outside distractions affects the validity and reliability of the test results. The present disclosure contemplates an immersive environment that reduces the intensity of outside distractions to advantageously improve testing. It is further contemplated in accordance with the present disclosure that a substantially non-immersive environment can reduce the intensity of outside distractions to improve testing, as will be discussed below.

To provide a much more immersive environment, the present invention includes using displays, sound systems and input devices which create a full environment for the subject to interact within. Immersive Virtual Reality Scenarios are those in which the subject feels as if they are actually in the environment to the extent that they may temporarily suspend their awareness of and sensitivity to the surrounding environment. The total immersion in a visual representation of a simulated reality, over time, enables the person to interact with it as if it were real. Such displays may include surrounding rooms and head mounted displays (HMD).

Surrounding rooms with projections, such as, for example, the Visiondome®, is available from Alternate Realities Corporation of Durham, N.C. In use, the subject is surrounded by a spherical dome typically 4–7 meters in diameter, with displays covering a full 180 degrees. Stereoscopic displays may be utilized in accordance with the present disclosure, which allow actual three dimension viewing of environments. Another system which may be used is provided by ImmersaDesk Pyramid Systems of Southfield, Mich., which offers the ImmersaDesk, a "drafting-table format prototype device. Using stereo LCD shutter glasses and magnetic head/hand tracking, this projection-based system offers a type of virtual reality that is extremely immersive and offers high-resolution color-correct "stereoscopic displays".

Head Mounted Displays (HMD) may also be used with the interactive computer generated simulated reality environment of the present disclosure, which may embody helmets in which optical equipment is built therein. The extent to which haptic capacity may be available is determined by the sophistication of the HMD. There are several manufacturers of HMD's ranging in cost from a few hundred dollars to thousands. One Example of an HMD is the Glasstron Model PLM-A55 available from Sony Corporation, or the V6 head mounted display available from Virtual Reality Source of Arvada, Colo.

Input devices include, for example, buttons, joysticks, mice, touch screens, touch pads, voice command recognition systems, eye movement and blink detectors, head movement detectors, and sensory and haptic gloves such as the Cyberglove® and the CyberTouch system, both produced by Virtual Technologies Incorporated and available from Virtual Reality Source of Arvada, Colo. Haptic gloves not only record a subjects movements and gestures, but also provides tactile feedback and object movement thus facilitating to a greater degree, a sense of playing the game in the actual setting or environment. Other input devices include hand gesturing input systems and head movement detection devices.

Other inputs from the subject can be monitored and input to the test scenario processor, as shown by arrow 20 including physiological monitoring equipment 22. These include measurements and changes in respiration, heart rate, blood pressure (Hoter Monitor), skin perspiration measurements, etc. In addition, head and hand trackers are available from for example, Polhemus Corporation of Colchester, Vt. The data is processed by appropriate physiological equipment 22 and input to the test scenario processor which includes computer 24 of system 10.

System 10 can use any general purpose computer 24, such as an Intel-based personal computer. A script database 26 stores and makes available predetermined test scenario scripts which describe and create the test environments and scenarios of the simulated reality environments. The test scenario processor includes test manager component 28 that processes the predetermined scripts and works in conjunction with the interactive computer generated simulated environment which includes a VR (Virtual Reality) simulation generator 30 (e.g. InterAct or Silicon Graphics system) to present the test on display system 12, as shown by arrow 18. Test manager component 28 responds to the subject actions, to cause changes in the environment through interaction with the VR Simulation generator 30. The test manager component 28 can also accept the physiological measurements from the physiological monitoring equipment 32 to cause changes in the environment.

A test administrator (not shown) can supervise the testing procedure through a separate monitor 29, which may be a separate computer, or a monitor connected to computer system 24 by direct cable or network. The test administrator can monitor the testing procedure if desired, or simply run automated testing.

Test manager component 28 records the subject's input and physiological measurements and interprets the results which includes determination of a neuropsychological dysfunction diagnosis. System 10 measures levels of executive functioning in the form of a diagnosis which can be output as summary scores. Summary scores can include: trials administered, total correct, total errors, % errors, perseverative responses, % perseverative responses, perseverative errors, % perseverative errors. Additional measures may include non-perseverative errors, % non-perseverative errors, conceptual level responses, % conceptual responses, categories completed, trials to complete first category, failure to maintain set, and learning to learn. Each of these can be used when computing summary scores and validity statistics.

The results are then output to test administrator's monitor 29, printed in hardcopy and/or sent as output to various media forms, electronic messaging, etc., as shown by results 32. The predetermined script database 26 can store the test responses for each subject as well as the analysis of the responses in results 32. The predetermined script database 26 can be stored by any means including, for example, flash memory, local or networked disk drives, optical or magneto-optical disks and tapes.

In an alternate embodiment, the test administrator can intervene with the testing procedure and modify system 10 via test administrator computer 29A, monitor 29 and keyboard 29B. Computer 29A is connected with system 10 and is configured for input from the system administrator for intervention with the testing for neuropsychological dysfunction. Input devices can include, such as, for example, those discussed above. At any time during the testing procedure, the test administrator may intervene with the testing procedure via computer 29A to modify the testing procedure of system 10. For example, during supervision through monitor 29 of a testing procedure, the test administrator may recognize particular patterns of responses, physiological measurements, etc., in relation to a particular predetermined test scenario script.

Using keyboard 29B, the test administrator may intervene and modify system 10 to alter testing conditions by changing the predetermined test scenario script, conditions of VR stimulation, limiting response and/or answer matching times, etc., independent of test manager 28 and within the test administrator's discretion. This feature of the present disclosure advantageously prevents response "coaching", non-relevant data, etc. It is envisioned that the interactive computer generated simulated reality environment may provide a plurality of questions to the subject and the test administrator may modify the questions in his/her discretion. It is further envisioned that the modification may include omission and/or alteration of particular questions. It is contemplated that system 10 includes a plurality of predetermined test scenarios and that the test administrator may substitute portions of the scenarios as part of a modification of the test.

The test administrator may also modify the testing procedure of system 10 upon recognition of perseverative responses by the subject.

The steps performed by one particular embodiment, in accordance with the present disclosure, as described above with regard to some of the contemplated embodiments of the components of system 10, is shown in FIG. 2. First, a predetermined script to test the subject is selected as depicted by step 100. This selection may be made based on the results of previously performed tests on the subject, including a standardized test, as will be described below. The subject is presented with the VR simulation in accordance with the predetermined script as depicted by step 102. As the subject reacts and interacts with the simulation, the subject's responses are recorded as depicted by step 104. If physiological measurements are also being monitored, they are similarly recorded.

Once the predetermined test scenario is complete, system 10 scores the results, as depicted by step 106. If other previous tests have been performed on the subject, they may be included in the scoring, as depicted by step 108, in phantom. Finally the results and interpretations are output as depicted by step 110 (results 32 shown in FIG. 1). The results can be in the form of a diagnosis which may include for example, statistical analysis, probability distribution, conclusion based on historical data or algorithms. Recommendation for further testing or possible treatments may be provided.

Alternatively, similar to that discussed above, at any time during the testing procedure for neuropsychological dysfunction of system 10, the test administrator may intervene and modify system 10 (step 112). During supervision of the testing procedure, as enumerated in the above referenced steps, the test administrator may recognize via monitor step 104, a particular pattern of responses, such as, for example, perseverations, extended duration for response and/or matching times, etc., in relation to the predetermined test scenario of step 100. The test administrator can modify the predetermined test scenario as depicted by step 112, and discussed above. It is contemplated that modification can include limitation of response and/or matching times.

An illustrative predetermined script presenting a test scenario will now be described. The script presents a computer card game called "Look for a Match" (LFAM). LFAM is designed to:

1. Assess a subject's capacity to form abstract concepts:
2. Assess a subject's capacity to maintain as well as shift from one principle to another.
3. Assess a subject's mental flexibility, including capacity to form abstract concepts and shift from one mental set to another with and without distractions.

The Immersive virtual reality and desktop scene is a gambling casino (for adults) and carnival for teenagers. The subject enters the casino/carnival and is invited to play "LFAM". The dealer will lay out four stimulus cards: the first will represent money items; the second illustrates an object found in the community; the third illustrates a mode of transportation; and the fourth will illustrate a personal item found in one's home. (There are two piles of 64 cards each and the player is to place each one according to the dealer's directions or until the dealer stops the game.)

The interactive computer generated simulated reality environment includes the background sound of muffled conversation and some additional occupied gambling tables pictured in the background. Upon entering the casino (carnival) the subject is immediately greeted by a dealer (barker), who speaks according to the following script:

"Hello. How are you? Please come to my table and play Let's Find A Match (LFAM). It's a lot of fun and you look like someone who will do well and enjoy it. In this game, though, I only can indicate a correct or incorrect choice. I cannot answer any questions or provide additional information once I give the directions.

"Here are the instructions: I will lay out four cards, face up. Then you will be given a pile of cards, face down. Please take only the top card and place it below the one facing up that you think it matches. Once you place it, it cannot be removed. Then, select the next card and so on. Please do not shuffle or rearrange the cards in any way. Take your time and enjoy the game. Speed is not counted for or against you.

"If you're ready, I'll place four cards down and then you can start playing." (The dealer shows the subject the deck from which he is to draw each card, and a duplicate deck is placed to the side for possible later use.) "All right? Let's play!"

Dealing the target cards:

1. The dealer turns up one card from each category. He puts the first card on the player's far left with the picture up and presented so it appears as it would have had the player actually turned it over. The card's background is white and it has in its center, one green five-dollar bill.

2. The second white card is placed immediately to the right of the first card facing the player. The card has two supermarkets printed on it and they are centered on the white card.

3. The third white card is placed immediately to the player's right of the second card facing the player. This card has three yellow propeller planes with each one placed at the corner of an invisible, though centered, triangle. The card faces the player.

4. The fourth white card is placed immediately to the right of the third, faces up, and has on it four purple refrigerators with one located in each corner of the card.

The play is as follows:

A. Once the dealer has laid out each target card, the player places each one under the target card where he/she thinks it belongs. The subject begins to play, and the dealer indicates whether the choice is correct or incorrect by ringing a bell. If the selection is incorrect, the dealer sounds a dull gong.

B. The first category is color. After ten correct placements in a row, the dealer shifts sets and indicates right or wrong by ringing the appropriate bell. The type of object is the second category, with the number of objects on a card being the third. Then the sets shift back to color, type of object and then number.

C. In both piles the cards are arranged so that they are turned over in the following order:
1. 1 red five dollar bill
2. 4 red propeller planes
3. 2 purple $5 bills
4. 1 red refrigerator
5. 4 green supermarkets
6. 1 yellow propeller plane
7. 4 purple $5 bills
8. 3 red refrigerators
9. 4 green propeller planes
10. 2 yellow refrigerators
11. 1 purple supermarket
12. 3 red $5 bills
13. 2 purple airplanes
14. 1 yellow supermarket
15. 3 green $5 bills
16. 4 purple refrigerators
17. 2 red supermarkets
18. 3 yellow refrigerators
19. 4 red $5 bills
20. 1 yellow refrigerators
21. 2 purple supermarkets
22. 3 green propeller planes
23. 2 yellow supermarkets
24. 3 purple $5 bills
25. 4 red supermarkets
26. 2 yellow $5 bills
27. 3 purple propeller planes
28. 4 red refrigerators
29. 2 green supermarkets
30. 1 red propeller plane
31. 4 green refrigerators
32. 1 red supermarket
33. 3 purple refrigerators
34. 4 yellow propeller planes
35. 1 green supermarket
36. 4 yellow $5 bills
37. 2 purple refrigerators
38. 3 yellow supermarkets
39. 1 green refrigerator
40. 4 purple propeller planes
41. 1 red $5 bill
42. 3 purple supermarkets
43. 4 yellow refrigerators
44. 2 green $5 bills
45. 3 red supermarkets
46. 2 yellow propeller planes
47. 1 purple refrigerator
48. 3 yellow $5 bills
49. 2 green propeller planes
50. 4 yellow supermarkets
51. 1 purple $5 bill
52. 3 green supermarkets
53. 2 red refrigerators
54. 4 green $5 bills
55. 1 purple propeller plane
56. 3 green refrigerators
57. 2 red propeller planes
58. 1 yellow $5 bill
59. 3 red propeller planes
60. 2 green refrigerators
61. 4 purple supermarkets
62. 3 yellow propeller planes
63. 2 red $5 bills
64. 1 green propeller plane D. When the "player" has made six runs of ten correct choices he is asked if he understands the principle of the game.

E. If the player exhausts his supply of cards prior to making six sets of ten correct choices, the second pack of cards is called into play.

F. However, if the player misplaces 30–40 cards in a row, than it is likely the player is unlikely to grasp the task.

G. If the player makes four correct runs, not withstanding the one or two attempts to match when the set changes, the dealer asks if the player knows the principle behind the game.

H. At card 32, a group of people walk by, with their conversation becoming louder as they get closer to the player. (This lasts through cards 32, 33, and 34.)

I. At card 42, the music begins to play with increasing loudness, reaching its highest volume at card 44. The sound diminishes over cards 45, 46, and 47.

J. At card 54, a couple passes by, stops next to the player, begins to chat and compliments him/her at how well he/she is doing. They leave by card 56.

K. If the player is continuing at card 72, a group of loud talking and laughing guests walk by and complete their pass by card 76.

L. At card 90, the lights dim because of a power surge, but the cards still can be seen. At card 93 the lights begin to return to their full brightness which is reached at card 96.

The LFAM script is scored as follows. The subject's responses are recorded by computerized recording by test manager 28, which notes the correctness/incorrectness of each response. Identical features on the stimulus and response cards are noted. (If color and number are the same, these two features are noted electronically.) Perseverative responses are noted. (In the WCST (Wisconsin Card Sorting Test, as produced by Robert Eaton), these were the most useful diagnostic indicators of frontal lobe deficit.) Perseverative responses to the initial, color match are evidenced by persistently making an unambiguously incorrect response, i.e., form or number, but not both.

Beyond the initial match of color, perseverative responses are those singular and unambiguous responses made in accordance to the previous set once the feature has been changed (i.e., continuing with color, when the set has shifted to type of object, or to number).

A "perseverative response exists" score begins with the first clear incorrect response is made, a second, but different incorrect set is selected, and the third incorrect selection matches the first incorrect one (i.e., the second incorrect response of three is different from the first and third which are identical and bracket the second). If the subject selects a category which is incorrect, the perseverative score begins with the first clear incorrect salaried response. (e.g., if the correct response is color, then the perseverative response must be repetitive numerical responses or repetitive/uninterrupted form responses. If three consecutive choices are made of an incorrect principle in a trial where there is a shift from correct to incorrect response, and then another shift to a category other than that which was previously chosen, it is a perseverative response.

Perseverative errors are those continuing responses which also are errors and are indicated as such. Scoring perseverations according to the illustrative embodiment includes recognizing that a perseveration is when the subject responds according to a previously correct rule or principle. Thus there must be a "Perseverative Principle" in order to score a perseveration. the most common way to derive a Perseverative Principle is when the rule shifts. At that time, the previously correct, but no longer appropriate rule is defined as the Perseverative Principle. An unambiguous (i.e. only matches one category) response that matches the previously correct response is scored as a perseveration. As an example, the subject correctly matches COLOR, and the rule shifts to FORM. If the subject makes a response that matches COLOR only, it is scored as a perseveration.

A perseveration may occur prior to the first correct series of 10 correct responses. If the subject makes an unambiguous incorrect response, while the response is not scored as a perseveration, that category becomes the "Perseverative Principle". If the subject then makes another unambiguous response to that category, it is scored as a perseveration.

The "Perseverative Principle" can change. If the subject makes three unambiguous incorrect responses in a row, then that category becomes the new "Perseverative Principle", and the second and third responses are scored as perseverations.

The scoring rules are as follows. Any unambiguous response that matches the "Perseverative Principle" is scored as a perseveration. Also, an ambiguous response that includes the previously correct rule may be scored as a perseveration, but only if it is bracketed by clear-cut perseverative responses. That is, if the subject (1) makes a perseverative response, then (2) an ambiguous response, if (3) the next response is also a perseveration, then the ambiguous response (2) is also scored as a perseveration. However, if the next response (3) is not a perseveration, then the ambiguous response is not scored as a perseveration. Also, non perseverative error scores involve subtracting the total perseverative error scores from the total score on the test.

This predetermined test scenario script and test results can be analyzed along with and in deference to other standard tests which help provide a full picture of a subject's functioning and deficits. Examples of other tests include the Motion History Questionnaire (Kennedy, R. S. & McCauley, M. E. 1984), a Simulator Sickness Questionnaire (Kennedy, R. S. & Lande, N. E. et al. 1993). These tests are administered to determine to what extent each individual has experienced and continues to be sensitive to motion. Such sensitivity is important to know and note vis-a-vis responses to desk top and immersive virtual reality environments.

Another helpful standard test is the Behavioral Assessment of the Dysexecutive Syndrome [BADS], (Wilson, Barbara A., et el. 1998), which, as a more ecologically valid, yet conventional test, more specifically measures the nature and extent the syndrome of deficits in executive functioning. Also, the Vineland Adaptive Behavioral Scale addresses the degree to which a subject displays age appropriate adaptive skills, and may be helpful for interpreting overall results when combined with the present invention.

The present invention runs on any general purpose computer, including personal computers, workstations and graphics intensive drivers. The scripts are coded in any computer language, including Lisp, C, C++, Java or specially designed graphics or scripting languages. The scripts and components can be stored in any standard database, including object-oriented databases and knowledge bases. Input from the physiological monitoring equipment may be preprocessed by techniques including preamplifiers, A/D (analog to digital) converters, VCO (voltage controlled oscillators), signal processing including DSP (digital signal processing) and compression/expansion algorithms. The input may be entered by communication ports, network connections, or specially created data signal inputs into the computer system.

Figure 3:
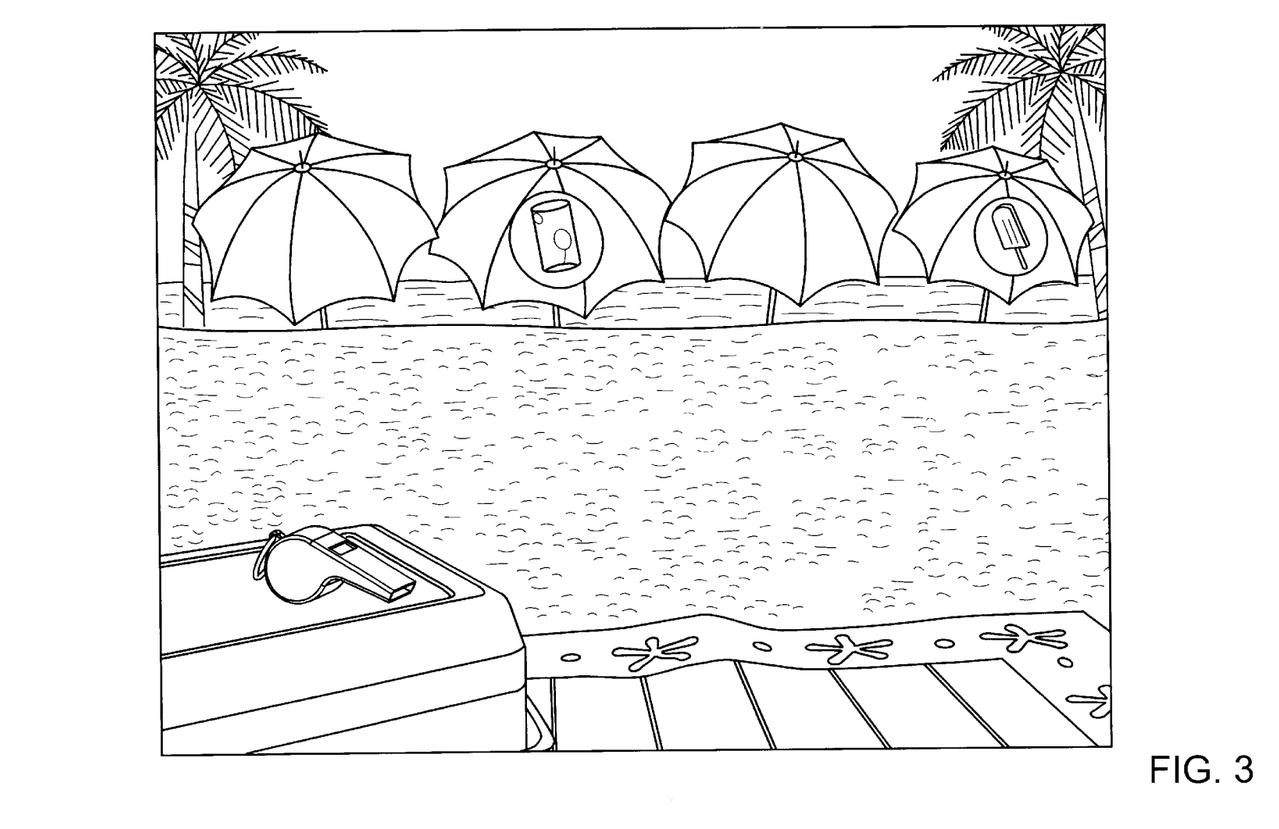
FIG. 3 is a sample image shown to a subject according to one embodiment of the present invention.

An alternate embodiment, similar to the format described above, of a predetermined test scenario associated with the computer card game called "Look for a Match" (LFAM) will now be described. The interactive computer generated simulated reality environment is based on a predetermined test scenario including a virtual reality scene that embodies a beach. The person initially views the beach from a distance and then slowly is brought to the scenario's main sight. The subject views four beach umbrellas under each of which sits one or two people. A sample image for this embodiment is shown in FIG. 3.

On the front panel of each umbrella, facing the subject, an object may be pictured, for example: (a) one green beach ball; (2) two red soda cans; (3) three blue frisbees; and (4) four yellow ices. Throughout the scenario there are ambient beach noises (muffled ocean and wind sounds, periodic conversational noises, children playing etc.).

The interactive computer generated simulated reality environment includes a virtual reality scene presented as a non-immersive, stereographic and three-dimensional computerized rendition of a beach scene. Participants wear lightweight stereographic eyewear that can be worn with or without regular eyeglasses (for those who cannot tolerate wearing the three dimensional eye glasses, the scene can be presented in a two dimensional rendition). There will be ambient beach and ocean sounds presented as they might occur at a regular beach.

The LFAM scenario advantageously demonstrates that real-life situations that identify and predict ecologically valid virtual scenes with greater accuracy. The virtual scenes in accordance with the present disclosure also predict that the impact of cognitive deficits on one's functioning in daily life activities.

As indicated above, the non-immersive virtual reality scene is a beach. As the person initially views the beach from a distance and they are slowly brought into the main scene of the test scenario. In particular, the main scene is one in which the subject/viewer looks out from his/her position under a beach umbrella towards the water. The subject views four beach umbrellas under each of which sits one or two people. On the front panel of each umbrella, facing the subject, is pictured an object: (a) one green beach ball; (2) two blue frisbees; (3) three red soda cans; and (4) four yellow ices. Throughout the scenario there are ambient beach noises (muffled sound of people talking, ocean, wind, periodic sounds of baby crying, children playing, etc.).

The testing proceeds according to the following predetermined test scenario script conducted by a commentator, not in view, and/or a cursor, both indicated herein as PROMPT (a description of the scene in parentheses):

PROMPT: Hello, welcome to the virtual beach today. You're here to help out with some deliveries. Let's move over here and I'll tell you what you'll be doing. (a viewpoint flies along a path and settles at the test scene area for the subject to view)

PROMPT: Well, here we are. (the instructions are repeated)

PROMPT: Look around . . . see those four umbrellas? (the cursor comes into view of the subject)

PROMPT: There are several people relaxing under different umbrellas. (the cursor points to each umbrella)

PROMPT: Each umbrella is different from the others, so you can tell the people apart. (the cursor comes back into view for the subject to answer the question)

A. INSTRUCTION SET 2 WHEN "SUBJECT INITIATED" IS SELECTED:

PROMPT: You need to click on the whistle sitting on the cooler to have an item presented. (the cursor points to the whistle for subject interaction)

PROMPT: Once presented you're to decide under which umbrella the objects should go. (the whistle animates as the cursor comes back into view of the subject)

PROMPT: Here we have some different objects that you'll be asked to deliver to those people. (the objects are shown one at a time until all are visible by the subject)

PROMPT: The problem is, each person wants different objects and I can't tell you which object goes to which person.

PROMPT: You're going to have to figure out the right match of objects to people and it isn't easy. (the objects exit from the view of the subject)

PROMPT: The people will let you know if the object you brought to them is the right one. (balls bounce into view of the subject and if "subject initiated" the whistle animates)

PROMPT: To deliver an object, just click on the umbrella to which you think it should be delivered. (the cursor visually points to an umbrella and clicks, the balls then sort)

PROMPT: Please try and get as many deliveries right as you can. (the cursor comes back into view of the subject)

PROMPT: The people will let you know right away if your delivery was correct or incorrect. (the sodas fly into view of the subject)

PROMPT: I'm afraid that's the only information you'll have in trying to figure out what to deliver to each person. (the cursor points to an umbrella and the sodas sort)

B. INSTRUCTION SET 2 WHEN "SUBJECT INITIATED" IS SELECTED:

PROMPT: After you've heard the response to your choice you need to click on the whistle again for the next item to be delivered. (the cursor points to the whistle and the whistle animates)

PROMPT: Remember your job is to get as many deliveries right as you can, good luck.(the cursor comes back into view of the subject)

PROMPT: I'll be back after you finish your deliveries. (the cursor leaves view of the subject)

PROMPT: If you'd like me to go over the directions again, please click on the bottom of the screen. (Red screen rises)

PROMPT: Otherwise, if you're ready to begin, click on the top half of the screen. (Green screen descends)

PROMPT: Let's begin (if green screen is selected)

PROMPT: Let's repeat. (if red screen is selected) (the next line is delivered at the end of the test)

PROMPT: Congratulations you've finished all the deliveries! Thanks for helping us out. (the sun slowly sets, and then the window goes black)

The interactive computer generated simulated reality environment provides various responses to correct and incorrect responses, such as, for example:

a. That's great, thanks.
b. Perfect!
c. Terrific, looks great.
d. Wonderful! Just what I wanted
e. That's perfect, Thanks
f. No way! Sorry!
g. That's not what I want!
h. No way, that's not what I asked for.
i. Oh no, that's not what I ordered!
j. Not what I want The interactive computer generated simulated reality environment includes various objects displayed from the panels of the umbrellas, such as, for example:

1. 1 red beach ball.
2. 4 red frisbees
3. 2 blue beach balls
4. 1 red popsicle
5. 4 green soda cans
6. 1 yellow frisbee
7. 4 blue beach balls
8. 3 red popsicles
9. 4 green frisbees
10. 2 yellow popsicles
11. 1 blue soda can
12. 3 ed beach balls
13. 2 blue frisbees
14. 1 yellow soda can
15. 3 green beach balls 16. 4 blue popsicles
17. 2 red soda cans
18. 3 yellow popsicles
19. 4 red beach balls
20. 1 yellow popsicle
21. 2 blue soda cans
22. 3 green frisbees
23. 2 yellow soda cans
24. 3 blue beach balls
25. 4 red soda cans
26. 2 yellow beach balls
27. 3 blue frisbees
28. 4 red popsicles
29. 2 green soda cans
30. 1 red frisbee
31. 4 green popsicles
32. 1 red soda can
33. 3 blue popsicles
34. 4 yellow frisbees
35. 1 green soda can
36. 4 yellow beach balls
37. 2 blue ices
38. 3 yellow soda cans
39. 1 green popsicle
40. 4 blue frisbees
41. 1 red beach ball
42. 3 blue soda cans
43. 4 yellow popsicles
44. 2 green beach balls
45. 3 red soda cans
46. 2 yellow frisbees
47. 1 blue popsicle
48. 3 yellow beach balls
49. 2 green frisbees
50. 4 yellow soda cans
51. 1 blue beach ball
52. 3 green soda cans
53. 2 red popsicles
54. 4 green beach balls
55. 1 blue frisbee
56. 3 green popsicles
57. 2 red frisbees
58. 1 yellow beach ball
59. 3 red frisbees
60. 2 green popsicles
61. 4 blue soda cans
62. 3 yellow frisbees
63. 2 red beach balls
64. 1 green frisbee The LFAM beach scene script is scored similar to that described above. The LFAM beach scene may be analyzed along with and in difference to other standardized tests, similar to those described.

Although the invention has been shown and described with respect to illustrative embodiments thereof, various other changes, omissions and additions in the form and detail thereof may be made therein without departing from the spirit and scope of the invention.

What is claimed is:

1. A system for diagnosing neuropsychological dysfunction comprising:
   at least one predetermined diagnostic scenario wherein distinct neuropsychological dysfunctions are determined;
   an interactive computer generated simulated environment based on said at least one predetermined diagnostic scenario; and
   a diagnostic scenario processor communicating with said interactive computer generated simulated environment and being configured to receive input from a subject interacting with said interactive computer generated simulated environment to determine a neuropsychological dysfunction diagnosis of said subject.

2. A system for diagnosing neuropsychological dysfunction as recited in claim 1, further comprising a test administrator input communicating with said [test] diagnostic scenario processor and being configured to receive input from a test administrator for modifying said at least one predetermined diagnostic scenario.

3. A system for diagnosing neuropsychological dysfunction as recited in claim 2, wherein said interactive computer generated simulated environment provides at least one question to said subject based on said at least one predetermined diagnostic scenario whereby said at least one question is modifiable by said test administrator.

4. A system for diagnosing neuropsychological dysfunction as recited in claim 3 wherein said interactive computer generated simulated environment provides a plurality of questions and said modification includes omission of a portion of said plurality of questions.

5. A system for diagnosing neuropsychological dysfunction as recited in claim 2 further comprising a plurality of predetermined test scenarios such that said test administrator may substitute portions of said plurality of predetermined diagnostic scenarios.

6. A system for diagnosing neuropsychological dysfunction as recited in claim 2, wherein said interactive computer generated simulated environment provides a plurality of questions to said subject based on said at least one predetermined diagnostic scenario and said test administrator modifies said plurality of questions when said input of said subject includes perseverations.

7. A system for diagnosing neuropsychological dysfunction as recited in claim 1, wherein said at least one predetermined diagnostic scenario includes a sequence of real life events and said interactive computer generated simulated environment provides at least one question to said subject based on said sequence of real life events.

8. A system for diagnosing neuropsychological dysfunction as recited in claim 7, wherein said sequence of real life events includes a beach scene.

9. A system for diagnosing neuropsychological dysfunction as recited in claim 1, wherein said at least one predetermined diagnostic scenario includes a sequence of non-reality events and said interactive computer generated simulated environment provides at least one question to said subject based on said sequence of non-reality events.

10. A system for diagnosing neuropsychological dysfunction as recited in claim 1, further comprising a plurality of predetermined diagnostic scenarios.

11. A system for diagnosing neuropsychological dysfunction as recited in claim 1, wherein said interactive computer generated simulated environment is substantially immersive.

12. A system for diagnosing neuropsychological dysfunction as recited in claim 1, wherein said interactive computer generated simulated environment is substantially non-immersive.

13. A system for diagnosing neuropsychological dysfunction as recited in claim 1, wherein said input received from said subject includes physiological measurements.

14. A system for diagnosing neuropsychological dysfunction comprising:
   a predetermined diagnostic scenario wherein distinct neuropsychological dysfunctions are determined, said scenario including a sequence of real life events;

an interactive computer generated simulated reality environment based on said predetermined diagnostic scenario, said interactive computer generated simulated reality environment providing a plurality of questions to a subject based on said sequence of real life events;

a diagnostic scenario processor communicating with said interactive computer generated simulated reality environment and being configured to receive input from said subject interacting with said interactive computer generated simulated reality environment to determine a neuropsychological dysfunction diagnosis of said subject; and a test administrator input communicating with said diagnostic scenario processor and being configured to receive input from a test administrator for modifying said predetermined diagnostic scenario.

15. A method for diagnosing executive dysfunction, the method comprising the steps of:

providing at least one predetermined test scenario wherein distrinct neuropsychological dysfunctions are determined;

producing an interactive computer generated simulated environment based on said at least one predetermined diagnostic scenario;

interacting the interactive computer generated simulated environment with a subject;

receiving input from said subject interacting with said interactive computer generated simulated environment by a diagnostic scenario processor communicating with said interactive computer generated simulated reality environment; and determining an executive dysfunction diagnosis of said subject based on said input received by said diagnostic scenario processor.

16. The method for diagnosing executive dysfunction as recited in claim 15, wherein the step of producing includes an interactive computer generated simulated environment which is substantially immersive.

17. The method for diagnosing executive dysfunction as recited in claim 15, wherein the step of producing includes an interactive computer generated simulated environment that is substantially non-immersive.

18. The method for diagnosing executive dysfunction as recited in claim 15, further including the step of receiving input from a test administrator for modifying said at least one predetermined diagnostic scenario.

19. The method for diagnosing as recited in claim 15, wherein the step of providing includes a predetermined diagnostic scenario having a sequence of real life events and said step of producing includes an interactive computer generated simulated environment providing a plurality of questions to said subject based on said sequence of real life events.

20. The method for diagnosing executive dysfunction as recited in claim 19, wherein the step of providing includes a predetermined diagnostic scenario having a sequence of real life events based on a beach scene.

* * * * *